(12) United States Patent
Lin (10) Patent No.: US 8,771,704 B2
(45) Date of Patent: Jul. 8, 2014

(54) DENGUE VACCINE, PHARMACEUTICAL COMPOSITION COMPRISING THE SAME, NUCLEOTIDE SEQUENCE AND ANTIBODY COMPOSITION

(75) Inventor: Yee-Shin Lin, Tainan (TW)

(73) Assignee: National Cheng Kung University, Tainan (TW)

( * ) Notice: Subject to any disclaimer, the term of this patent is extended or adjusted under 35 U.S.C. 154(b) by 125 days.

(21) Appl. No.: 13/230,209

(22) Filed: Sep. 12, 2011

(65) Prior Publication Data

US 2012/0070454 A1    Mar. 22, 2012

(30) Foreign Application Priority Data

Sep. 13, 2010 (TW) .............................. 99130862 A (51) Int. Cl.
*A61K 39/295* (2006.01)
*A61K 39/12* (2006.01)

(52) U.S. Cl.
USPC .................................... 424/202.1; 424/218.1

(58) Field of Classification Search
None
See application file for complete search history.

(56) References Cited

U.S. PATENT DOCUMENTS

2006/0159699 A1* 7/2006 Howley et al. ............. 424/199.1

OTHER PUBLICATIONS

Youn et al., J. Virology, Jun. 30, 2010, 84(18):9516-9532.*
John R. Stephenson, Understanding dengue pathogenesis: implications for vaccine design, Bulletin of the World Health Organization, 2005, vol. 83, Iss. 4, p. 308-314, World Health Organization.
Mei-Chun Chen, Chiou-Feng Lin, Huan-Yao Lei, Shih-Chao Lin, Hsiao-Sheng Liu, Trai-Ming Yeh, Robert Anderson and Yee-Shin Lin, Deletion of the C-terminal region of dengue virus nonstructural protein 1 (NS1) abolishes anti-NS1-mediated platelet dysfunction and bleeding tendency, The Journal of Immunology, 2009, vol. 183, pp. 1797-1803, The American Association of Immunologists.

* cited by examiner

*Primary Examiner* — Stacy B. Chen
(74) *Attorney, Agent, or Firm* — Bacon & Thomas, PLLC (57) ABSTRACT

The present invention relates to a dengue vaccine, a pharmaceutical composition comprising the same, a nucleotide sequence, and an antibody composition. The dengue vaccine of the present invention includes chimeric nonstructural protein 1, which comprises N-terminus of DV NS1 from amino-acid residues 1 to 270 and C-terminus of JEV NS1 from amino-acid residues 271 to 352 (designated DJ NS1). Therefore, the dengue vaccine without autoimmunity according to the present invention is able to avoid cross-reactions with endothelial cells and platelets, and is able to shorten the bleeding time.

5 Claims, 4 Drawing Sheets

DENGUE VACCINE, PHARMACEUTICAL COMPOSITION COMPRISING THE SAME, NUCLEOTIDE SEQUENCE AND ANTIBODY COMPOSITION

CROSS REFERENCE TO RELATED APPLICATION

This application claims the benefits of the Taiwan Patent Application Serial Number 099130862, filed on Sep. 13, 2010, the subject matter of which is incorporated herein by reference.

BACKGROUND OF THE INVENTION

1. Field of the Invention

The present invention relates to a dengue vaccine, a pharmaceutical composition comprising the same, a nucleotide sequence and an antibody composition, more particularly, to a dengue vaccine which causes no autoimmunity and is depleted of cross-reactivity with endothelial cells and platelets, a pharmaceutical composition comprising the same, a nucleotide sequence and an antibody composition.

2. Description of Related Art

Dengue fever, also called breakbone fever, is an acute infectious disease induced by the propagation of dengue viruses (DV) via *Aedes aegypti* or *Aedes albopictus* and its symptoms include high fever (39° C. to 40° C.) or aversion to cold, skin rash, fatigue in limbs, muscle pain, frontal headache, retro-orbital pain, abdominal pain, backache (hence the term breakbone fever), sore throat, and maybe vomiting and fainting. The commonly mentioned dengue virus is classic dengue fever, also called primary dengue fever. In addition, severe and life-threatening dengue fever characterized by hemorrhage or shock may be developed, also called dengue hemorrhagic fever (DHF) or dengue shock syndrome (DSS), or secondary dengue.

It is estimated that there are about 50 million to 100 million cases of dengue infection worldwide each year, with about 250,000 to 500,000 cases of dengue hemorrhagic fever. In other words, two-fifths of the world's population is at risk from dengue infection. Hence, the prevention and treatment of dengue fever is an important issue for the governments of many countries. However, the mechanism underlying dengue disease is not clearly understood. Furthermore, neither effective and safe vaccines nor drugs on specific treatment of diseases caused by dengue viruses are available so far. Since dengue virus is the major pathogen of dengue disease, the early detection or prevention with effective vaccine can efficiently control morbidity and death rates of dengue fever.

Recently, numerous strategies of dengue vaccine design are based on the neutralizing efficacy of antibodies against viral envelope (E) or nonstructure (NS) protein. Although the E protein is responsible for eliciting major neutralizing antibodies during DV infection, it is also associated with the induction of antibody dependent enhancement (ADE). Antibody dependent enhancement (ADE) is a complicating factor in dengue vaccine development in that the pre-existing antibodies raise concerns of causing more severe disease. In contrast, antibodies against the NS1 protein are able to kill DV-infected cells by complement-mediated cell lysis and thus are not associated with ADE. A limitation to the vaccine strategy of NS1, however, is that anti-NS1 antibodies may cause cross-reaction with endothelial cells and platelets, and thus may negatively influence coagulation function, resulting in prolonged bleeding time. The side effect of autoimmunity caused by the vaccine still has not been resolved.

Therefore, it is desirable for the technical field to develop a novel vaccine which does not induce antibody dependent enhancement and autoimmunity, is depleted of cross-reactivity with endothelial cells and platelets, and is able to shorten bleeding time.

SUMMARY OF THE INVENTION

The major object of the present invention is to provide a dengue vaccine, which includes chimeric nonstructural protein 1 (DJ NS1). The chimeric DJ NS1 includes: N-terminus of DV NS1 from amino acids 1 to 270 and C-terminus of JEV NS1 from amino acids 271 to 352.

The vaccine of the present invention targets dengue virus nonstructural protein 1 (DV NS1) to avoid the potential risk of antibody dependent enhancement (ADE). The epitopes that cause autoimmunity from DV NS1 are truncated and further combined with C-terminus of JEV NS1 from amino acids (aa) 271 to 352 to form the chimeric DJ NS1, which has enhanced stability, high antigenicity and causes no autoimmunity, and thus can be used as a non-harmful vaccine with protection effect. Moreover, through the result of the passive immunization tests, it can be confirmed that the anti-chimeric DJ NS1 antibody/antibody composition according to the present invention has the effect of treating dengue disease.

In the dengue vaccine according to the present invention, the amino acid sequence similarity between the chimeric DJ NS1 and the SEQ ID NO: 1 in the sequence listing preferably is 90% or more, and more preferably is 95% or more.

In the dengue vaccine according to the present invention, the amino acid sequence of the chimeric DJ NS1 is preferred to be amino acid sequence of SEQ ID NO: 1.

In the dengue vaccine according to the present invention, the N-terminus (aa 1-270) of the dengue virus nonstructural protein 1 (DV NS1) preferably is derived from dengue virus protein.

In the dengue vaccine according to the present invention, the C-terminus (aa 271-352) of the Japanese encephalitis virus nonstructural protein 1 (JEV NS1) preferably is derived from Japanese encephalitis virus protein.

In the dengue vaccine according to the present invention, preferably, the dengue vaccine can be used to prevent dengue hemorrhagic fever or dengue shock syndrome.

The present invention further provides a dengue vaccine-containing pharmaceutical composition. The dengue vaccine includes chimeric nonstructural protein 1 (DJ NS1), and the chimeric DJ NS1 includes: N-terminus of DV NS1 from amino acids 1 to 270 and C-terminus of JEV NS1 from amino acids 271 to 352.

The dengue vaccine-containing pharmaceutical composition according to the present invention includes the chimeric DJ NS1, such that the cross-reactions with endothelial cells and platelets can be avoided to shorten bleeding time. In addition, the chimeric DJ NS1 has enhanced stability, high antigenicity and causes no antibody dependent enhancement and autoimmunity.

In the dengue vaccine-containing pharmaceutical composition according to the present invention, the amino acid sequence similarity between the chimeric DJ NS1 and the SEQ ID NO: 1 in the sequence listing preferably is 90% or more, and more preferably is 95% or more.

In the dengue vaccine-containing pharmaceutical composition according to the present invention, the chimeric DJ NS1 preferably has the amino acid sequence of SEQ ID NO: 1.

Preferably, the dengue vaccine-containing pharmaceutical composition according to the present invention can be used to treat or prevent dengue hemorrhagic fever or dengue shock syndrome.

The present invention also provides a nucleotide sequence that encodes chimeric DJ NS1. The chimeric DJ NS1 includes: N-terminus of DV NS1 from amino acids 1 to 270, and C-terminus of JEV NS1 from amino acids 271 to 352.

The chimeric DJ NS1 encoded from the nucleotide sequence of the present invention can be used as a dengue vaccine, such that the cross-reactions with endothelial cells and platelets can be reduced and the bleeding time can be shortened. In addition, the chimeric DJ NS1 has enhanced stability, high antigenicity, and causes no antibody dependent enhancement and autoimmunity.

The nucleotide sequence of the present invention preferably is SEQ ID NO: 2 in the sequence listing.

Preferably, the nucleotide sequence of the present invention can be used to produce a dengue vaccine.

The present invention further provides an antibody composition for binding to chimeric DJ NS1. The chimeric DJ NS1 includes: N-terminus of DV NS1 from amino acids 1 to 270, and C-terminus of JEV NS1 from amino acids 271 to 352.

The antibody composition of the present invention can be used to treat dengue disease, more particularly dengue hemorrhagic disease. Through the result of the passive immunization tests, it can be confirmed that the anti-chimeric DJ NS1 antibody/antibody composition according to the present invention has the effect of treating dengue disease. The antibody composition according to the present invention can shorten bleeding time, show reduced cross-reactivity with endothelial cells and platelets, and cause no antibody dependent enhancement and autoimmunity.

In the antibody composition for binding to chimeric DJ NS1 according to the present invention, the chimeric DJ NS1 preferably has the amino acid sequence of SEQ ID NO: 1.

In the antibody composition for binding to chimeric DJ NS1 according to the present invention, preferably, the antibody composition can be obtained by injecting an animal with a chimeric DJ NS1-containing vaccine and then purifying the sera from the animal.

DETAILED DESCRIPTION OF THE PREFERRED EMBODIMENT

Mice

C3H/HeN mice were obtained from The Jackson Laboratory and maintained on standard laboratory food and water in the Laboratory Animal Center of National Cheng Kung University Medical College. Their 8-wk-old progeny were used for the experiments; Housing, breeding, and experimental use of the animals were performed in strict accordance with the Experimental Animal Committee in National Cheng Kung University.

[Platelet Preparation]

Human whole blood containing anticoagulant (29.9 mM sodium citrate, 113.8 mM glucose, 72.6 mM NaCl, and 2.9 mM citric acid (pH 6.4)) was centrifuged at 100×g for 20 min at room temperature to obtain platelet-rich plasma (PRP). The platelet-rich plasma was centrifuged at 1000×g for 10 min at room temperature and washed in EDTA/PBS buffer twice. The washed platelets were suspended in Tyrode's solution (137 mM NaCl, 20 mM HEPES, 3.3 mM $NaH_2PO_4$, 2.4 mM KCl, 1 mg/ml BSA, and 5.6 mM glucose (pH 7.4)) at a concentration of $10^8$ platelets/ml.

[cDNA]

Dengue type 2 (New Guinea C strain) virus grown in BHK21 cells was available from National Institute of Preventive Medicine, Department of Health, and cDNA were obtained. *Escherichia coli* BL-21(DE3) pLysS strain bearing the plasmid pRSET-DVNS1 was used to express recombinant proteins of DV NS1 and was provided from Shiau's lab (Dr. Ai-Li Shiau) of Department of Microbiology and Immunology of National Cheng Kung University (Taiwan). *Escherichia coli* BL-21(DE3)pLysS strain bearing the plasmid pET-32a(+)-JNS1 was used to express recombinant proteins of JEV NS1 and was available from Hsieh's lab (Dr. Shie-Liang Hsieh) of Department of Microbiology and Immunology of Yang-Ming University (Taiwan) and Lin's lab (Yi-Ling Lin) of Institute of Biomedical Science Academia Sinica (Taiwan).

[DJ NS1 from cDNA]

Primers A and C were used to amplify full-length DV-NS1 from the pPRSET-DVNS1.

Subsequently, primers D and F were used to amplify full-length JEV-NS1 from the pET-32a(+)-JNS1.

The full-length JEV-NS1 was used as a template, and primers E and F were used to amplify the C terminus of JEV-NS1 from amino acids (aa) 271 to 352 from the full-length JEV-NS1.

Then, the C terminus of JEV-NS1 from amino acids 271 to 352 and DV-NS1 were mixed as templates, and primers A and F were used to amplify DJ NS1 containing the N-terminus of DV NS1 from aa 1 to 270, and C terminus of JEV-NS1 from aa 271 to 352.

The obtained DJ NS1 was further used as a template, and primers A, F', A' and F were used to amplify DJ NS1 with cohesive ends.

The above-mentioned primers for PCR were listed as follows.

《Primer》
Primer A:
(SEQ ID NO: 3)
5'-AATTCGATAGTGGTTGCGTTGTAAGC-3';

Primer A':
(SEQ ID NO: 4)
5'- CGATAGTGGTTGCGTTGTAAGC-3';

Primer C:
(SEQ ID NO: 5)
5'-TCGAGCTAGGCTGTGACCAAGGAGTTAAC-3';

Primer C':
(SEQ ID NO: 6)
5'- GCTAGGCTGTGACCAAGGAGTTAAC-3';

Primer D:
(SEQ ID NO: 7)
5'-AATTCGACACTGGATGTGCCATTGAC-3';

Primer D':
(SEQ ID NO: 8)
5'- CGACACTGGATGTGCCATTGAC-3';

Primer E:
(SEQ ID NO: 9)
5'-TAGCAGGACCATGGCATTTAAATGGCATAGTCTTGGACT
TTGAC-3';

-continued

Primer F:
(SEQ ID NO: 10)
5'-TCGAGCTAAGCATCAACCTGTGATCTAAC-3'; and

Primer F':
(SEQ ID NO: 11)
5'- GCTAAGCATCAACCTGTGATCTAAC-3'.

PCR primers and reaction enzymes (including DNA polymerase, T4 polynucleotide kinase) were placed into two centrifuge tubes, respectively, and uniformly mixed to perform a denaturation step (95° C. for 5 min) and a renaturation step (65° C. for 10 min). After the primers A, F', A' and F were used to amplify DJ NS1, about 25% of PCR products was DJ NS1 with cohesive ends containing EcoRI and XhoI restriction sites. The ligation was accomplished by insertion of the DJ NS1 with cohesive ends into a vector (pET28a).

[Recombinant Protein and Antibody Preparation]

JEV NS1, DV NS1, and chimeric DJ NS1 (consisting of N-terminus of DV NS1 from aa 1-270 and C-terminus of JEV NS1 from aa 271-352) cDNA were cloned into the above-mentioned vector with histidine-tag. Plasmids were introduced into *Escherichia coli* BL21. The recombinant proteins were induced by 1 μM isopropyl B-D-1-thiogalactopyranoside (Calbiochem) and purified with $Ni^{2+}$ columns. Subsequently, proteins were examined using 10% SDS-PAGE. Proteins from SDS-PAGE were excised and homogenized in adjuvant to immunize mice. Purified protein (25 μg) was emulsified in CFA for the first immunization, and 2 wk later in IFA for 2, 3 or 4 immunizations every week. Mouse sera were collected 3 days after the last immunization, and IgG was purified using protein G columns (Pharmacia Fine Chemicals).

[Antibody Binding to Platelet Assay]

Washed platelets were fixed with 1% formaldehyde in PBS at room temperature for 10 min and then washed with PBS. Various doses of anti-full-length DV NS1, anti-JEV NS1 or anti-chimeric DJ NS1 were incubated with platelets for 30 min. After washing, platelets were incubated with FITC-conjugated anti-mouse IgG (Jackson ImmunoResearch Laboratories) for 30 min. Antibody binding to platelets was analyzed using flow cytometry, as shown in FIG. 1.

Figure 1:
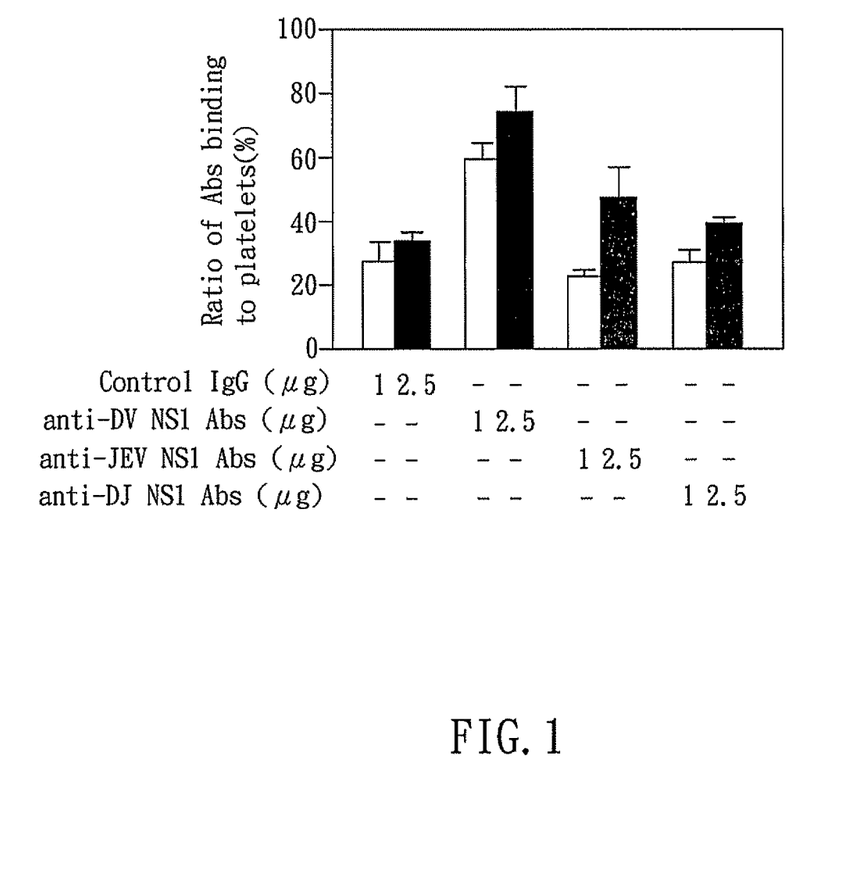
FIG. 1 shows the results of antibody binding to platelet assay in vitro according to one preferred example of the present invention.

As shown in FIG. 1, the binding ability of anti-DJ NS1 antibody to human platelets was lower than that of anti-full-length DV NS1 antibody and similar to that of control IgG and anti-JEV NS1.

[Bleeding Time]

Actively immunized mice with full-length DV NS1, chimeric DJ NS1 and JEV NS1 proteins, and normal control mice without above-mentioned proteins were tested on bleeding time. Bleeding time was performed by a 3-mm tail-tip transection. Blood droplets were collected on filter paper every 30 s for the first 3 min, and every 10 s thereafter. Bleeding time was recorded when the blood spot was smaller than 0.1 mm in diameter. The results are shown in FIG. 2.

Figure 2:
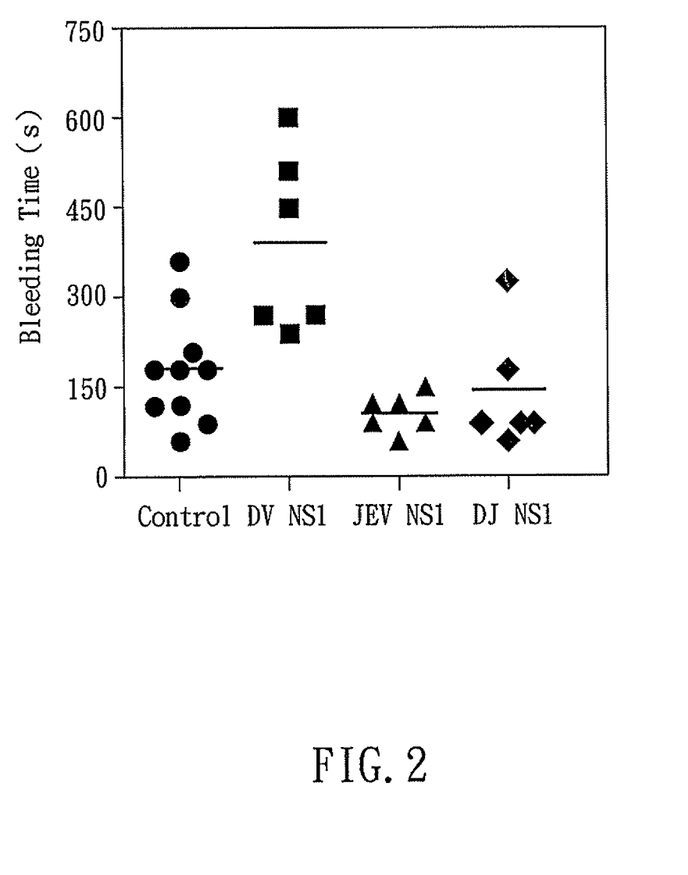
FIG. 2 shows the results of bleeding time tests on actively immunized mice according to one preferred example of the present invention.

As shown in FIG. 2, the bleeding time in chimeric DJ NS1-immunized mice was shorter than that in full-length DV NS1-immunized mice, and similar to that in normal control mice and JEV NS1-immunized mice. The results showed that the dengue vaccine of chimeric DJ NS1 according to the present invention indeed has the effect for shortening bleeding time.

[Effect of Antibody-Animal Model]

Passively immunized mice with anti-full-length DV NS1, anti-JEV NS1 and anti-chimeric DJ NS1 antibodies, and normal control mice without any antibodies and viruses were tested on bleeding time. Bleeding time was performed by a 3-mm tail-tip transection. Blood droplets were collected on filter paper every 30 s for the first 3 min, and every 10 s thereafter. Bleeding time was recorded when the blood spot was smaller than 0.1 mm in diameter. The results are shown in FIG. 3.

Figure 3:
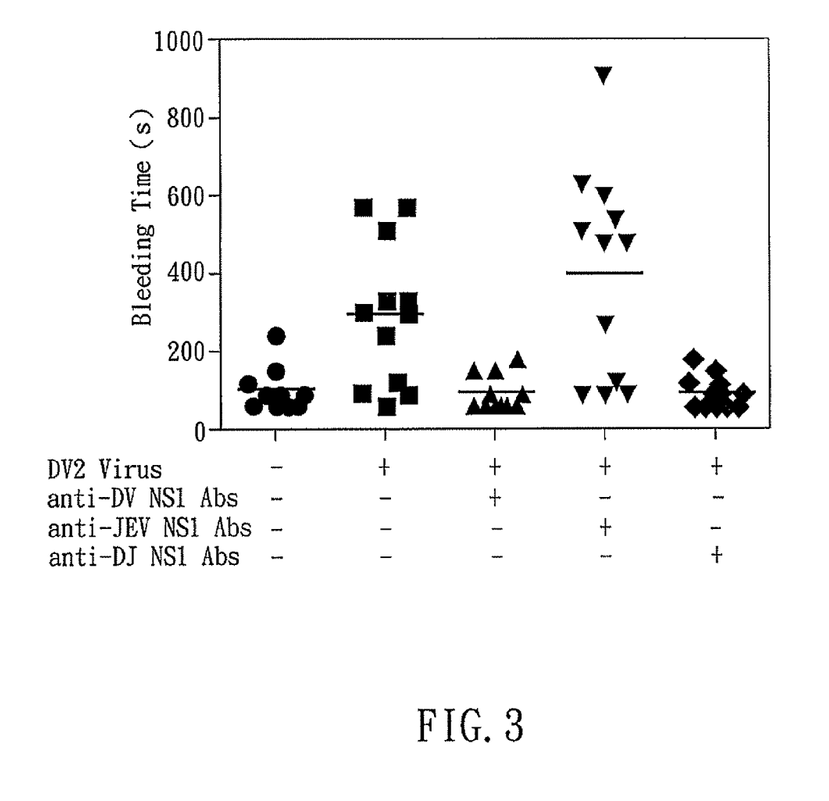
FIG. 3 shows the results of bleeding time tests on infected mice according to one preferred example of the present invention.

In FIG. 3, the columns in sequence from left to right are the first group to the fifth group, wherein the normal control mice without administering any antibodies and viruses were classified into the first group (as a control group), the mice administered with dengue virus but no antibodies were classified into the second group, the mice administered with dengue virus and anti-DV NS1 antibody were classified into the third group, the mice administered with dengue virus and anti-JEV NS1 antibody were classified into the fourth group, and the mice administered with dengue virus and anti-DJ NS1 antibody were classified into the fifth group. As shown in FIG. 3, the fifth group of mice, which were immunized with anti-DJ NS1 antibody, showed significantly shorter bleeding time, compared to the second group of mice, which were infected by dengue virus but not immunized with any antibodies. In addition, the fifth group of mice showed similar bleeding time to the first group of mice without administering any antibodies and viruses.

It can be confirmed that the anti-chimeric DJ NS1 antibody (or antibody composition) of the present invention indeed has the effect for treating dengue disease.

[Antibody Binding to Endothelial Cell Assay]

Figure 4:
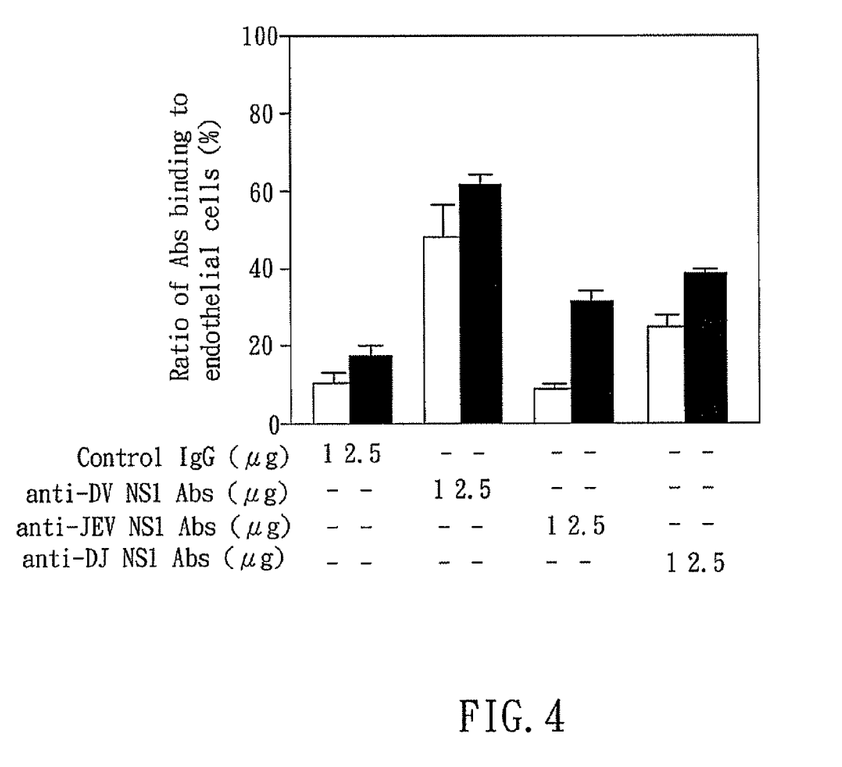
FIG. 4 shows the results of antibody binding to endothelial cell assay in vitro according to one preferred example of the present invention.

The human microvascular endothelial cell line (HMEC-1) was available from Center for Disease Control and Prevention, Atlanta. Ga. The cells were cultured at 37° C. and washed by PBS, followed by the addition of trypsin-EDTA, and reacted for several minutes. Then, the cells were resuspended in a fresh serum-containing medium in an appropriate amount. After centrifugation, the cells were fixed with 1% formaldehyde in PBS for 10 min and then washed with PBS. Diluted antibodies in an appropriate dose were incubated with the cells for 1 hr. After washing with PBS for three times, the cells were incubated with FITC-conjugated secondary antibodies for 1 hr. The amount of antibody binding to endothelial cells was analyzed using flow cytometry, as shown in FIG. 4.

The results showed that the binding ability of the anti-chimeric DJ NS1 antibody according to the present invention to endothelial cells was significantly lower than that of anti-full-length DV NS1 antibody. Therefore, it can be confirmed that the anti-chimeric DJ NS1 antibody according to the present invention does not cause autoimmunity.

The present invention takes dengue virus nonstructural protein 1 (DV NS1) as a vaccine target protein, and modifies DV NS1 by gene recombination to obtain a chimeric DJ NS1. The chimeric DJ NS1 of the present invention includes N-terminus of DV NS1 from amino acids 1 to 270 and C-terminus of JEV NS1 from amino acids 271 to 352. Accordingly, the chimeric DJ NS1 according to the present invention can prevent the potential risk of antibody dependent enhancement (ADE). In addition, the present invention truncates the epitopes that cause autoimmunity from DV NS1 and combines it with C-terminus of JEV NS1 from amino acids 271 to 352 to thus obtain the chimeric DJ NS1. The obtained chimeric DJ NS1 has enhanced stability, high antigenicity and causes no autoimmunity, and hence can be used as a non-harmful vaccine with protection effect.

Furthermore, through the bleeding time test on the passively immunized mice, it can be confirmed that the chimeric DJ NS1 according to the present invention has the effect of treating dengue disease.

The above examples are intended for illustrating the embodiments of the subject invention and the technical features thereof, but not for restricting the scope of protection of the subject invention. The scope of the subject invention is based on the claims as appended.

What is claimed is:

1. A composition comprising a chimeric nonstructural protein DJ NS1, wherein the chimeric nonstructural protein DJ NS1 comprises:
- a sequence having at least 95% sequence identity with the N-terminus of the dengue virus nonstructural protein 1 (DV NS1) from amino acids 1 to 270 of SEQ ID NO: 1; and
- a sequence having at least 95% sequence identity with the C-terminus of Japanese encephalitis virus nonstructural protein 1 (JEV NS1) from amino acids 271 to 352 of SEQ ID NO: 1.

2. A composition comprising a chimeric nonstructural protein DJ NS1, wherein the chimeric nonstructural protein DJ NS1 comprises an amino acid sequence having at least 95% sequence identity with SEQ ID NO: 1.

3. The composition of claim 1, wherein the amino acid sequence of the chimeric nonstructural protein DJ NS1 is SEQ ID NO: 1.

4. The composition of claim 1, wherein the N-terminus of the dengue virus nonstructural protein 1 (DV NS1) from amino acids 1 to 270 is derived from dengue virus protein.

5. The composition of claim 1, wherein the C-terminus of the Japanese encephalitis virus nonstructural protein 1 (JEV NS1) from amino acids 271 to 352 is derived from Japanese encephalitis virus protein.

* * * * *

SEQUENCE LISTING

<160> NUMBER OF SEQ ID NOS: 11

<210> SEQ ID NO 1
<211> LENGTH: 352
<212> TYPE: PRT
<213> ORGANISM: Artificial
<220> FEATURE:
<223> OTHER INFORMATION: Recombinant protein containing N-terminus of Dengue Virus (aa 1-270) and C-terminus of Japanese encephalitis virus (aa 271-352)

<400> SEQUENCE: 1

```
Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
    50                  55                  60

Asn Leu Met Trp Lys Gln Ile Thr Pro Glu Leu Asn His Ile Leu Ser
65                  70                  75                  80

Glu Asn Glu Val Lys Leu Thr Ile Met Thr Gly Asp Ile Lys Gly Ile
                85                  90                  95

Met Gln Ala Gly Lys Arg Ser Leu Arg Pro Gln Pro Thr Glu Leu Lys
            100                 105                 110

Tyr Ser Trp Lys Thr Trp Gly Lys Ala Lys Met Leu Pro Thr Glu Ser
        115                 120                 125

His Asn Gln Thr Phe Leu Ile Asp Gly Pro Glu Thr Ala Glu Cys Pro
    130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Arg Glu Lys Gln Asp
                165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
        195                 200                 205

Thr Trp Lys Ile Glu Lys Ala Ser Phe Ile Glu Val Lys Ser Cys His
    210                 215                 220

Trp Pro Lys Pro His Thr Leu Trp Ser Asn Gly Val Leu Glu Ser Glu
225                 230                 235                 240

Met Ile Ile Pro Lys Asn Phe Ala Gly Pro Val Ser Gln His Asn Tyr
                245                 250                 255

Arg Pro Gly Tyr His Thr Gln Thr Ala Gly Pro Trp His Leu Asn Gly
            260                 265                 270

Ile Val Leu Asp Phe Asp Tyr Cys Pro Gly Thr Lys Val Thr Ile Thr
        275                 280                 285

Glu Asp Cys Gly Lys Arg Gly Pro Ser Val Arg Thr Thr Thr Asp Ser
    290                 295                 300

Gly Lys Leu Ile Thr Asp Trp Cys Cys Arg Ser Cys Ser Leu Pro Pro
305                 310                 315                 320

Leu Arg Phe Arg Thr Glu Asn Gly Cys Trp Tyr Gly Met Glu Ile Arg
                325                 330                 335

Pro Val Arg His Asp Glu Thr Thr Leu Val Arg Ser Gln Val Asp Ala
            340                 345                 350
```

<210> SEQ ID NO 2
<211> LENGTH: 1056
<212> TYPE: DNA
<213> ORGANISM: Artificial
<220> FEATURE:
<223> OTHER INFORMATION: Cloned DNA containing N-terminus of Dengue
      virus (aa 1-270) and C-terminus of Japanese encephalitis virus
      (aa 271-352)

<400> SEQUENCE: 2

```
gatagtggtt gcgttgtgag ctggaaaaac aaagaactga agtgtggcag tgggattttc      60
atcacagaca acgtgcacac atggacagaa caatacaagt tccaaccaga tccccttca     120
aaactagctt cagctatcca gaaagctcat gaagagggca tttgtggaat ccgctcagta    180
acaagactgg aaaatctgat gtggaaacaa ataacaccag aattgaatca cattctatca    240
gaaaatgagg tgaagttgac tattatgaca ggagacatca aggaatcat gcaggcagga     300
aaacgatctc tgcggcccca gcccactgag ctgaagtatt catggaaaac atggggcaaa    360
gcgaaaatgc tccctacaga gtctcataac cagaccttc tcattgatgg ccccgaaaca     420
gcagaatgcc ccaacacaaa cagagcttgg aattcgctgg aagttgaaga ctatggcttt    480
ggagtattca ccaccaatat atggctaaag ttgagagaaa agcaggatgt attctgcgac    540
tcaaaactca tgtcagcggc cataaaagac aacagagccg tccatgccga tatgggttat    600
tggatagaaa gtgcactcaa tgacacatgg aagatagaga agcctctttt catcgaagtt    660
aaaagctgcc actggccaaa gccacacacc ctctggagta atggagtgct agaaagtgag    720
atgataattc caagaattt cgctggacca gtgtcacaac acaactacag accaggctac    780
catacacaaa cagcaggacc atggcatcta aatggcatag tcttggactt tgactattgc    840
ccagggacaa aagtcaccat tacagaggat gtgtggcaaga gaggcccttc ggtcagaacc    900
actactgaca gtggaaagtt gatcactgac tggtgctgtc gcagttgctc ccttccgccc    960
ctacgattcc ggacagaaaa tggctgctgg tacggaatgg aaatcagacc tgttaggcat   1020
gacgaaacaa cactcgttag atcacaggtt gatgct                              1056
```

<210> SEQ ID NO 3
<211> LENGTH: 26
<212> TYPE: DNA
<213> ORGANISM: Artificial
<220> FEATURE:
<223> OTHER INFORMATION: Synthetic primer

<400> SEQUENCE: 3

```
aattcgatag tggttgcgtt gtaagc                                           26
```

<210> SEQ ID NO 4
<211> LENGTH: 22
<212> TYPE: DNA
<213> ORGANISM: Artificial
<220> FEATURE:
<223> OTHER INFORMATION: Synthetic primer

<400> SEQUENCE: 4

```
cgatagtggt tgcgttgtaa gc                                               22
```

<210> SEQ ID NO 5
<211> LENGTH: 29
<212> TYPE: DNA
<213> ORGANISM: Artificial
<220> FEATURE:

<223> OTHER INFORMATION: Synthetic primer

<400> SEQUENCE: 5
tcgagctagg ctgtgaccaa ggagttaac         29

<210> SEQ ID NO 6
<211> LENGTH: 25
<212> TYPE: DNA
<213> ORGANISM: Artificial
<220> FEATURE:
<223> OTHER INFORMATION: Synthetic primer

<400> SEQUENCE: 6
gctaggctgt gaccaaggag ttaac         25

<210> SEQ ID NO 7
<211> LENGTH: 26
<212> TYPE: DNA
<213> ORGANISM: Artificial
<220> FEATURE:
<223> OTHER INFORMATION: Synthetic primer

<400> SEQUENCE: 7
aattcgacac tggatgtgcc attgac         26

<210> SEQ ID NO 8
<211> LENGTH: 22
<212> TYPE: DNA
<213> ORGANISM: Artificial
<220> FEATURE:
<223> OTHER INFORMATION: Synthetic primer

<400> SEQUENCE: 8
cgacactgga tgtgccattg ac         22

<210> SEQ ID NO 9
<211> LENGTH: 44
<212> TYPE: DNA
<213> ORGANISM: Artificial
<220> FEATURE:
<223> OTHER INFORMATION: Synthetic primer

<400> SEQUENCE: 9
tagcaggacc atggcattta aatggcatag tcttggactt tgac         44

<210> SEQ ID NO 10
<211> LENGTH: 29
<212> TYPE: DNA
<213> ORGANISM: Artificial
<220> FEATURE:
<223> OTHER INFORMATION: Synthetic primer

<400> SEQUENCE: 10
tcgagctaag catcaacctg tgatctaac         29

<210> SEQ ID NO 11
<211> LENGTH: 25
<212> TYPE: DNA
<213> ORGANISM: Artificial
<220> FEATURE:
<223> OTHER INFORMATION: Synthetic primer

<400> SEQUENCE: 11
gctaagcatc aacctgtgat ctaac         25